United States Patent
Röhlcke et al.

(10) Patent No.: US 6,394,800 B1
(45) Date of Patent: May 28, 2002

(54) DEVICE FOR PROCESSING ORDERS FOR SUPPLYING ORTHODONTIC BANDS

(75) Inventors: Friedrich-Wilhelm Röhlcke, Kämpfelbach-Bilfingen; Hans-Peter Schorpp, Ettlingen; Karl-Heinz Griesbeck, Karlsruhe, all of (DE)

(73) Assignee: Dentaurum J. P. Winkelstroeter KG, Ispringen (DE)

( * ) Notice: Subject to any disclaimer, the term of this patent is extended or adjusted under 35 U.S.C. 154(b) by 0 days.

(21) Appl. No.: 09/320,863

(22) Filed: May 27, 1999

Related U.S. Application Data

(63) Continuation of application No. PCT/EP97/06895, filed on Dec. 10, 1997.

(30) Foreign Application Priority Data

Dec. 10, 1996 (DE) .......................... 196 51 223

(51) Int. Cl.[7] .............................. A61C 3/00; G06F 17/60
(52) U.S. Cl. .......................................... 433/23; 433/24
(58) Field of Search ........................ 351/178; 345/420; 235/375, 380; 433/3, 7, 27, 32, 23, 24; 29/896.11; 705/2, 22, 23–24, 26–29; G06F 17/60; A61C 3/00

(56) References Cited

U.S. PATENT DOCUMENTS

| | | | |
|---|---|---|---|
| 4,817,024 A | * 3/1989 | Saigoh .......................... | 703/1 |
| 4,991,305 A | * 2/1991 | Saigo et al. .................. | 33/507 |
| 5,040,975 A | * 8/1991 | Ettwein et al. ................ | 433/3 |
| 5,238,402 A | * 8/1993 | Rohlcke et al. ............... | 433/23 |
| 5,326,259 A | * 7/1994 | Rohlcke et al. ............... | 433/8 |
| 5,472,344 A | * 12/1995 | Binder et al. ................. | 433/7 |
| 5,485,399 A | * 1/1996 | Saigo et al. .................. | 351/178 |
| 5,528,021 A | * 6/1996 | Lassus et al. | |
| 6,068,482 A | * 5/2000 | Snow ......................... | 433/223 |
| 6,213,767 B1 | * 4/2001 | Dixon et al. .................. | 433/9 |

FOREIGN PATENT DOCUMENTS

| | | | | |
|---|---|---|---|---|
| DE | 3727102 | * 8/1987 | ........... | A61C/3/00 |
| DE | 19651223 A1 | * 6/1998 | ........... | G06F/17/60 |
| EP | 0 576 268 | 12/1993 | | |
| EP | 951249 A1 | * 10/1999 | ........... | A61C/7/00 |
| WO | WO 94/10935 | 5/1994 | | |
| WO | 9825537 A1 | * 6/1998 | ........... | A61C/7/00 |

OTHER PUBLICATIONS

Snow et al., Interactive computer technologies in dentistry, Health Care in the Information Age, IOS Press and Ohmsha, 1996, pp.411–421 (Chapter 48).*

* cited by examiner

Primary Examiner—Cuong H. Nguyen
(74) Attorney, Agent, or Firm—Leydig, Voit & Mayer, Ltd.

(57) ABSTRACT

The invention proposes a novel device for processing orders for supplying orthodontic bands having orthodontic functional parts fitted as specified in the orders, comprising:

a computer unit having a memory for managing basic data for the unequipped orthodontic bands, basic data for the functional parts that are to be welded on, and data for the bands equipped with one or more functional parts specifically as well as graphics data sets allocated to the unequipped and equipped bands and to the functional parts;

an input device for inputting the data for an order for a band having a functional part fitted as specified in the order or functional parts fitted as specified in the order; and a printer unit for printing out an order acknowledgement and for printing labels with order data and a graphical representation of the band equipped as specified in the order.

18 Claims, 4 Drawing Sheets

| Order design | Tooth | Front | Back | Band group | Article 1<br>Article 2<br>Order | Mouth position<br>Tooth position | Angulation<br>Band<br>Position | Special request 1<br>Special request 2 |
|---|---|---|---|---|---|---|---|---|
| 12 / 000 15 | 2. BICUSPID | d-⊕-m (g/o) | m-⊕-d (g/o) | 8601 | 713-007-00<br>Edgewise Bracket -7' T.0' A..018"<br>750-602-10<br>Double bracket, short | BUCCAL<br>PALATINAL | CENTRAL | 0° |
| 13 / 000 25 | 2. BICUSPID | d-⊕-m (g/o) | m-⊕-d (g/o) | 8601 | 713-007-00<br>Edgewise Bracket -7' T.0' A..018"<br>750-602-10<br>Double bracket, short | BUCCAL<br>PALATINAL | CENTRAL | 0° |
| 20 / 000 45 | 2. BICUSPID | d-⊕-m (o/g) | m-⊕-d (o/g) | 8611 | 714-621-00<br>Edgewise Bracket -22' T.0' Ang.018"<br>750-602-10<br>Double bracket, short | BUCCAL<br>LINGUAL | CENTRAL | 0° |
| 21 / 000 35 | 2. BICUSPID | d-⊕-m (o/g) | m-⊕-d (o/g) | 8611 | 714-621-00<br>Edgewise Bracket -22' T.0' Ang.018"<br>750-602-00<br>Double bracket, short | BUCCAL<br>LINGUAL | CENTRAL | 0° | a b c d e f

Doctor: Dr. Thomas
55566 SOBERNHEIM

ASD design : 00028 / 000

System:   16 Standard Edgewise .018" technology
11 Central

8450   GR. 14

726-103-00
Buccal 750-602-10
Palatinal

QTY: 5000   000158/13712345/05.06.1996

FIG. 5

| Order design | Tooth | Front | Back | Band group | Article 1 Article 2 Order | Mouth position Tooth position | Angulation Band Position | Special request 1 | Special request 2 |
|---|---|---|---|---|---|---|---|---|---|
| 12 / 000 | 15 2. BICUSPID | 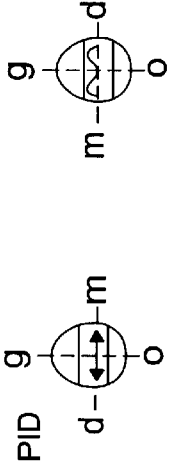 | 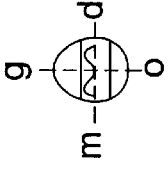 | 8601 | 713-007-00<br>Edgewise Bracket -7' T.0' A..018"<br>750-602-10<br>Double bracket, short | BUCCAL<br><br>PALATINAL | 0°<br><br>CENTRAL | | |
| 13 / 000 | 25 2. BICUSPID | 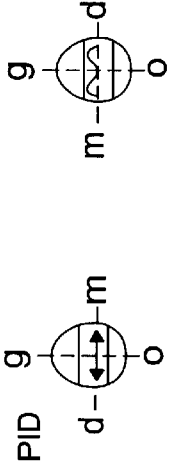 | 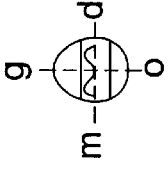 | 8601 | 713-007-00<br>Edgewise Bracket -7' T.0' A..018"<br>750-602-10<br>Double bracket, short | BUCCAL<br><br>PALATINAL | 0°<br><br>CENTRAL | | |
| 20 / 000 | 45 2. BICUSPID | 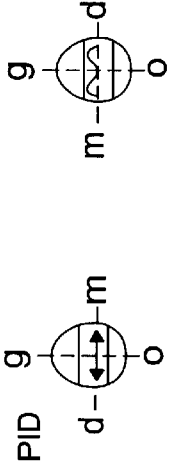 | 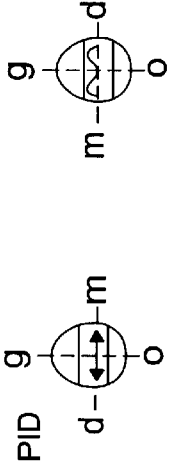 | 8611 | 714-621-00<br>Edgewise Bracket -22' T.0' Ang.018"<br>750-602-10<br>Double bracket, short | BUCCAL<br><br>LINGUAL | 0°<br><br>CENTRAL | | |
| 21 / 000 | 35 2. BICUSPID | 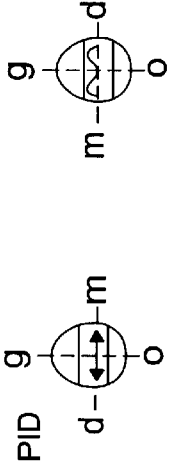 | 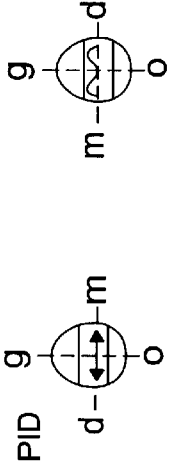 | 8611 | 714-621-00<br>Edgewise Bracket -22' T.0' Ang.018"<br>750-602-00<br>Double bracket, short | BUCCAL<br><br>LINGUAL | 0°<br><br>CENTRAL | | |

DEVICE FOR PROCESSING ORDERS FOR SUPPLYING ORTHODONTIC BANDS

This appln is a cont of PCT/EP97/06895 filed Dec. 10, 1997.

The invention relates to a device for processing orders for supplying orthodontic bands having orthodontic functional parts fitted as specified in the orders.

The novel and inventive device is intended, in particular, to allow such orders to be processed in considerably less time, and at the same time to provide greater reliability for processing the orders in house.

Until now, the aforementioned orders were normally registered using data processing and stored in coded, machine-readable form.

In parallel with this, the orders were given to the appropriate department for carrying out these orders, and the bands and functional parts were removed from stocks as specified in the orders and gathered together for processing. A suitable package was selected for the finished order and provided with a label, which generally contained only a brief printed description of the packaged bands with functional parts.

A disadvantage of this type of processing for orders for supplying orthodontic bands having orthodontic functional parts fitted as specified in the orders is that the definition of the order, which was always provided only in words and numbers, meant that quickly registering the type of order and, accordingly, also quickly and reliably checking the order carried out and comparing it with the original order was time-consuming and sometimes prone to error.

In addition, for the doctor supplied with the bands having orthodontic functional parts fitted as specified in an order, and his staff, allocating the goods received to their own stocks and/or to a patient to be treated is difficult owing to the lack of information and the small structures of the functional parts fitted. Furthermore, particularly in the case of the orthodontic functional parts fitted as specified in an order, the so-called angulation angle at which they are fitted on the band is frequently of great importance, and relatively small differences in angle can be assessed sufficiently reliably on the equipped band only with difficulty or not at all.

The novel device for processing orders for supplying orthodontic bands having orthodontic functional parts fitted as specified in the orders avoids the above disadvantages by comprising:

a computer unit having a memory for managing basic data for the unequipped orthodontic bands, basic data for the functional parts that are to be welded on, and data for the bands equipped with one or more functional parts specified as well as graphics data sets allocated to the unequipped and equipped bands and to the functional parts;

an input device for inputting the data for an order for a band having a functional part fitted as specified in the order or functional parts fitted as specified in the order; and a printer unit for printing out an order acknowledgement and for printing labels with order data and a graphical representation of the band equipped as specified in the order.

In this arrangement, the computer unit checks the order data input using the input device to determine whether they correspond to the data for a stored band with specific parts fitted.

Owing to the fact that graphics data sets are held ready, in particular for the bands equipped with functional parts, and that a label with such a graphics representation is produced automatically, the information needed for processing the order is given to those persons involved in order processing and checking in such a way that it can be registered quickly and reliably. At the same time, the label printed with the graphics representation allows the doctor receiving the dispatch to allocate it to a particular stock and/or to a particular patient much more easily.

In addition, the printer unit can be used to produce design instructions as specified in an order, as well as repeat-order forms, which can be enclosed with the bands when they are delivered to the customer.

In addition, and to ensure even more reliability, it is possible to provide for the computer unit to be able to use the printer unit to print out an order acknowledgement containing a graphical representation of the band having one or more functional parts, which was ordered with the specific parts fitted. Consequently, the person ordering or customer receives a graphical acknowledgement of his order and is able to check the order data very quickly and reliably and to correct it if necessary.

The check instigated by the computer unit for the order data input using the input device can lead to the computer unit causing a graphics data set assigned to the band specified in the order to be created, specifically if the check establishes that an appropriate graphics data set does not yet exist in the management memory.

The bands can be equipped with functional parts by means of a welding process, in particular spot welding, soldering or other equivalent joining techniques.

The graphics data sets used according to the invention for the bands and the functional parts can be recorded and/or processed photographically, using computer-aided design (CAD) or in another way.

The essential feature is that the graphics representation of a band equipped as specified in the order is assembled from the graphics data sets.

All in all, the graphics data sets, assembled to form a graphical representation, for a band and the associated functional parts offer a much better optical information aid than a simple photographic representation of the equipped band would be able to, because the functional parts can in each case be represented, in particular, such that their main characteristics can be seen clearly and are easy for the observer to register.

Order processing can be rationalised further in that the device additionally comprises a stores management system for automatically controlled removal of the band and the functional part or functional parts needed for dealing with the order, selecting a suitable package and bringing together the band, the functional part or functional parts and the package with the order-specific label printed by the printer unit in a transport container.

A further increase in speed can be achieved in that the input device comprises a data telecommunication interface which a customer uses to transmit the order data to the computer unit directly in machine-readable form. In this arrangement, it is possible to provide for the reply or the order confirmation to be transmitted back to the customer via the data telecommunication interface as well, and for it to contain not only the specific order described in words and numbers, but also the associated graphics data set, so that the customer receives an order acknowledgement with an added graphic, virtually online, and is able to check it and make corrections as necessary.

Allocation of the packaged bands with specific parts fitted at the customer's premises to already existing stocks and/or to the materials for treating a specific patient can be simplified further in that the labels which the printer unit has printed with order data and a graphical representation of the band equipped as specified in the order additionally contain the name of the patient to be treated with the band, possibly in encrypted form, or another identifier specific to the customer. This provides maximum reliability, for the customer as well, in ensuring that the ordered bands with specific parts fitted are actually used for the intended patient or are placed into stock correctly.

The stores management system is preferably equipped with a handling device which, on the basis of the order to be processed, effects removal of the band and the functional part or parts needed for dealing with the order from corresponding band and functional-part stocks.

In this instance, a further provision which may be made is that the corresponding bands and possibly also the functional parts bear a machine-readable marking, for example a laser marking, which the handling device can check, during removal, for the identification to be established in agreement with the basic data provided in accordance with the order.

In addition, the printer unit can be designed such that it can produce a label, for the transport container, whose wording can be read by a machine and which, on the transport container, makes it possible for a machine to be able to locate the transport container in the course of production by reading the label. An automatic reply can then be sent to the computer unit, so that it is possible for the transport container and hence also the progress of the order processing to be precisely checked and documented at each stage of order processing.

The invention also relates to a method for processing orders for supplying orthodontic bands, which can be carried out using the device described above according to the invention.

This method firstly comprises inputting the data for an order for a band having a functional part which is to be welded on as specified in the order into a computer unit, the computer unit checking whether the order data corresponds to the data stored in the memory for bands with specific parts fitted, printing labels with order data and a graphical representation of the band specified in the order, and removal of the bands and functional parts needed for dealing with the order from a corresponding stock. In addition, it is possible for a suitable package to be selected automatically and for the band, the functional part and the package with the order-specific label printed by the printer unit to be brought together automatically in a transport container. The transport container with all these individual parts then goes to the department carrying out the fitting work and can then be transported further, together with the completed order, for checking and goods dispatch.

These and further advantages of the invention are explained in even more detail below with reference to the drawing, in which, specifically, FIG. 1 shows a block diagram relating to the method according to the invention;

FIG. 5 shows an example of a design instruction produced according to the invention.

Figure 1:
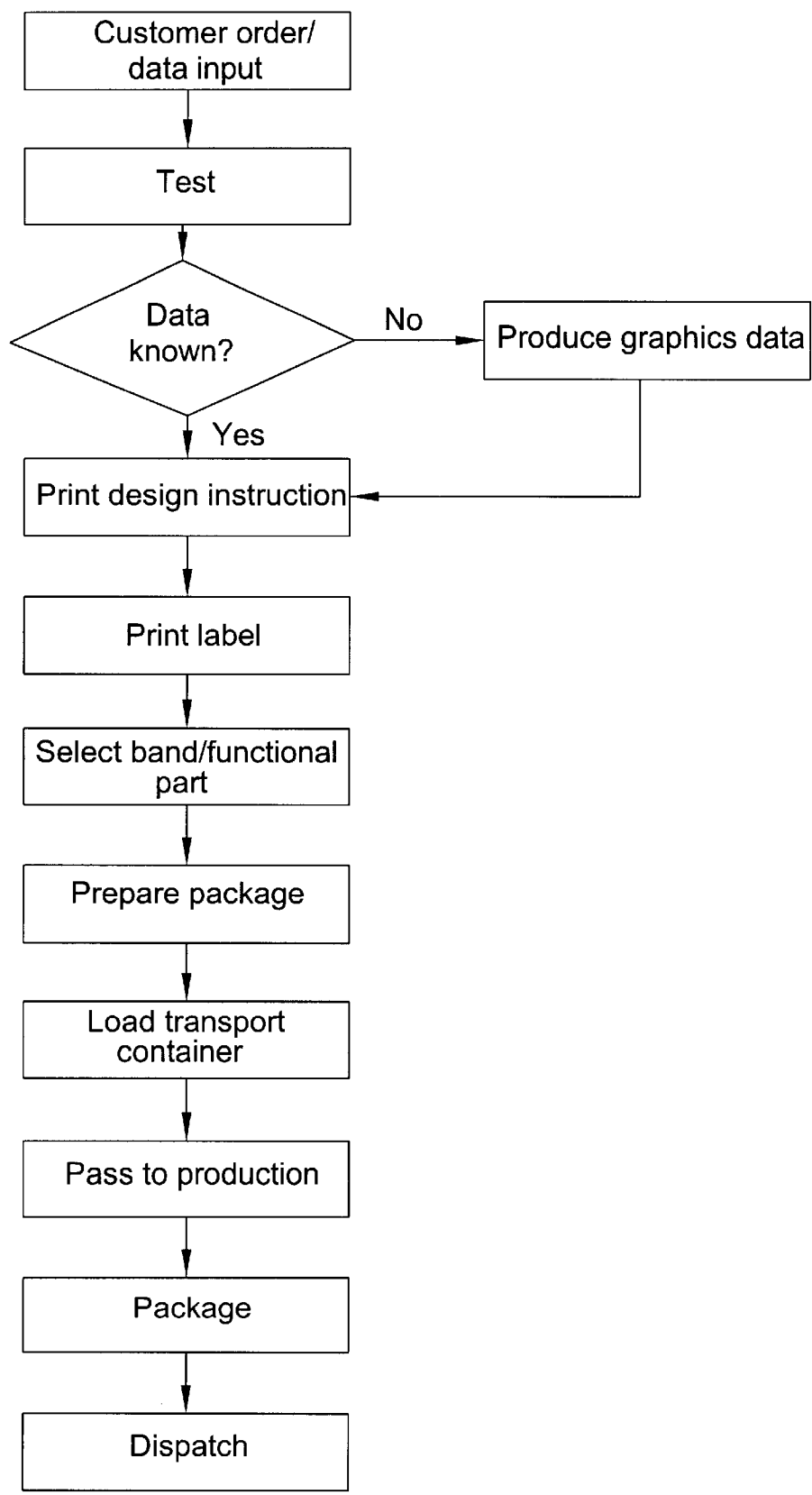

The method according to the invention, shown in the flow chart in the block diagram in FIG. 1, comprises data input, after the customer order has been received, into the computer unit to be used according to the invention, which then carries out a check to determine whether the order data are known and can be correlated to graphics data. Should the graphics data be missing from the memory of the computer unit, a graphics data set is produced in a separate step and, otherwise, the procedure passes directly to printing a design order automatically. Subsequently, a label is printed out, which, if the printing unit comprises both a printer for the design instructions and a printer for printing the labels, can naturally also take place at the same time as the design instruction is printed, or possibly even before the design instruction is printed out.

The band which is to be equipped and the functional parts to be attached to the band are then selected, and the package is prepared and loaded into a transport container and subsequently passed to production. After production, i.e. equipping the band on the basis of the design instruction, the equipped band is then packaged and sent for dispatch.

Figure 2:
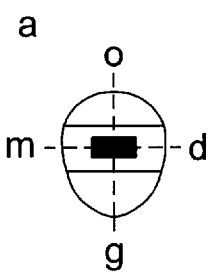
FIG. 2 shows examples of graphics representations to be used according to the invention.
Figure 2:
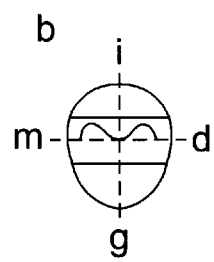
Figure 2:
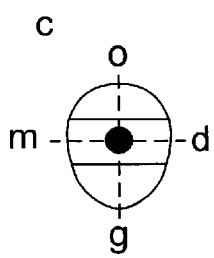
Figure 2:
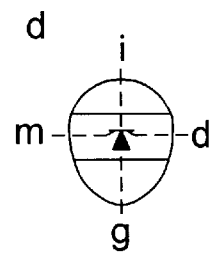
Figure 2:
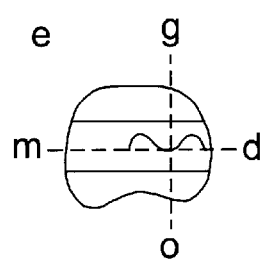
Figure 2:
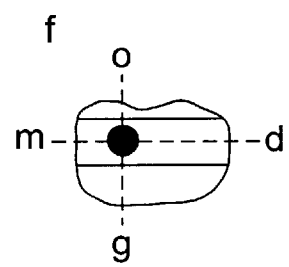

FIG. 2 shows the graphics representations, to be used when printing the design instruction and when printing the label, for the equipped bands, with the letters having the following meanings: m=mesial, d=distal, o=occlusal, g=gingival and i=incisal. At the same time, the shape of the bands in the graphics representation shows whether they are a top jaw band or a bottom jaw band and, similarly, whether the band is a molar band, a band for front teeth etc.

The picture of the band also shows the functional part in a graphically abstract manner, a so-called cover plate being arranged in a central position in FIG. 2a, for example, as indicated by the central arrangement of the symbol for the cover plate in the reticule.

In FIG. 2b, the functional part mounted on the band is a so-called double bracket, likewise in a central position, as indicated by the central orientation of the symbol for the double bracket in the reticule.

The functional part shown in FIG. 2c is a so-called knob, likewise in a central position again. The functional part shown in FIG. 2d on the band in a central position is a lingual/palatinal bracket, and FIG. 2e shows a double bracket, but in the distal position.

Finally, the functional part shown in FIG. 2f is again a knob, but in the mesial position.

Figure 3:
FIG. 3 shows further examples of graphics representations to be used according to the invention.

Other examples of graphics representations of equipped bands are shown in FIG. 3, FIG. 3a showing a band for a central right front tooth, fitted with an attachment with zero-degree angulation. The zero-degree angulation is indicated here by a double arrow.

FIG. 3b shows the same front tooth band with an attachment which, however, is welded on with an angulation which is not equal to zero degrees, indicated by the oblique arrow direction.

The graphics representations shown in FIGS. 2 and 3 are produced, as specified in an order, from basic data and associated graphics data sets for the respective bands and from basic data and associated graphics data sets for the functional parts, depending on the customer order for bands with specific parts fitted, and are automatically printed out on the design instruction and likewise shown on the label to be used for the package.

Figure 4:
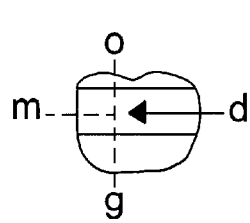
FIG. 4 shows a package label printed according to the invention.
Figure 4:
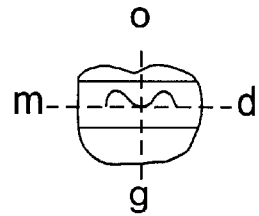

Such a label to be used for the package is shown in FIG. 4 and can, as shown, contain the name and address of the doctor to receive the delivery, article numbers, system notes and, finally, the graphics data produced according to the invention and any other information which may be desired.

In the context of the present invention, it is important that graphics representations made up from graphics data sets are printed on the label and indicate the contents of the package not only to those persons processing the order, but also, in particular, to the recipient, in a manner which can easily be registered.

Finally, FIG. 5 shows an example of a design instruction produced according to the invention, which, by way of example, can also have a quantity column and can be used, in the form shown or in a similar form, as a repeat-order form.

What is claimed is:

1. A device for processing an order for supplying orthodontic bands having orthodontic functional parts fitted as specified in said order containing data, comprising a computer unit having a memory for managing basic data for unequipped orthodontic bands, basic data for the functional parts that are to be fitted to the unequipped orthodontic bands, and orthodontic bands equipped with specific functional parts as well as graphics data sets allocated to the unequipped and equipped orthodontic bands and to the functional parts, an input device for inputting the data for an order for a band having a functional part fitted as specified in the order, wherein the computer unit checks the order data input using the input device to determine whether it corresponds to the data for a stored band with specific parts fitted, and a printer unit for printing labels with said order data and a graphical representation of the orthodontic band equipped as specified in the order.

2. The device according to claim 1, wherein the printer unit is designed such that it can be used to produce a design instruction, an order acknowledgement and/or a repeat-order form.

3. The device according to claim 1, wherein the device comprises a stores management system for automatically controlled removal of the band and the functional part needed for dealing with the order from appropriate stocks.

4. The device according to claim 3, wherein the stores management system comprises the function of selecting a suitable package and bringing together the band, the functional part or parts and the package with the order-specific label printed by the printer unit in a transport container.

5. The device according to claim 1, wherein a check of the order data establishing that the order data does not correspond to any stored data for orthodontic bands with specific parts fitted causes a corresponding data set including an associated graphics data set to be compiled.

6. The device according to claim 1, wherein the input device comprises a data telecommunication interface.

7. The device according to claim 1, wherein the labels which the printer unit has printed with order data and a graphical representation of the band equipped as specified in the order contains, in printed form, the name of the patient to be treated with the band and/or the name of the doctor treating the patient.

8. The device according to claim 4, wherein the printer unit produces a label, for the transport container, that can be read by a machine.

9. The device according to claim 1, wherein the printer unit produces a design instruction and/or an order acknowledgement and/or repeat-order forms which comprise a graphical representation of the band indicated in the order.

10. A method for processing an order for supplying orthodontic bands having orthodontic functional parts fitted as specified in the order, comprising following steps:

inputting data for an order for a band having a functional part fitted as specified in the order using an input device into a computer unit which comprises a memory for managing the basic data for unequipped orthodontic bands, basic data for the functional parts that are welded on, and orthodontic bands equipped with specific functional parts as well as graphics data sets allocated to the unequipped orthodontic bands and to the functional parts;

comparing the order data, input using the input device, in the computer unit with the data for the stored orthodontic bands with specific parts fitted, and allocation of the stored graphics data to the order data input;

using a printer unit to print a label with order data and a graphical representation of the band equipped as specified in the order, and removing of the band and functional part needed for dealing with the order from a stock, wherein said band and said functional part correspond to the order data and graphical representation.

11. The method according to claim 10, wherein the printer unit is used to produce a design instruction, an order acknowledgement and/or a repeat-order form.

12. The method of claim 10, wherein said removal of the band and functional part needed for dealing with the order from a stock is automatically effected by a stores management system that controls the removal of the band and the functional part needed for dealing with the order from appropriate stocks.

13. The method of claim 12, wherein the stores management system automatically adds to a transport container a suitable package, the band, the functional part or parts and an order-specific label printed by the printer unit.

14. The method of claim 10, wherein a comparison of the order establishing that the order data does not correspond to any stored data for orthodontic bands with specific parts fitted automatically causes a corresponding data set including an associated graphics data set to be compiled.

15. The method of claim 10, wherein input of the data for an order using an input device into a computer unit comprises telecommunication.

16. The method of claim 10, wherein the printer unit also prints the name of the patient to be treated with the band and/or the name of the doctor treating the patient in addition to the order data and a graphical representation of the band equipped as specified in the order.

17. The method of claim 13, wherein the stores management system comprises a transport container, and the transport container bears a label that can be read by a machine.

18. The method of claim 10, wherein the printer unit prints a repeat-order form which comprises a graphical representation of the specifically equipped band indicated in the order.

* * * * *